United States Patent [19]

Bequette et al.

[11] 4,436,738

[45] Mar. 13, 1984

[54] STABILIZED ESTRADIOL CREAM COMPOSITION

[75] Inventors: Robert J. Bequette; Linda G. Hobbs; Joseph A. Scott, all of Evansville, Ind.

[73] Assignee: Mead Johnson & Company, Evansville, Ind.

[21] Appl. No.: 358,068

[22] Filed: Mar. 15, 1982

[51] Int. Cl.$^3$ ............................................. A61K 31/56
[52] U.S. Cl. ...................................................... 424/238
[58] Field of Search ......................................... 424/238

[56] References Cited

U.S. PATENT DOCUMENTS

| | | | |
|---|---|---|---|
| 2,096,744 | 10/1937 | Hildebrandt et al. | 260/397.4 |
| 4,154,820 | 5/1979 | Simoons | 424/238 |
| 4,344,940 | 8/1982 | Chew et al. | 424/238 |

OTHER PUBLICATIONS

Martin et al., Obstet. Gynecol., vol. 39, pp. 771–774, (1972), (1/19).
Schiff et al., Fert. Steril., 28/10, (1977), (1/21), pp. 1063–1066.
Rigg et al., J. Clin. Endocr. Metab., (1977), No. 45/6, pp. 1261–1264.

*Primary Examiner*—Elbert L. Roberts
*Attorney, Agent, or Firm*—Richard P. Ryan; Robert H. Uloth

[57] ABSTRACT

Loss of potency of estradiol cream compositions found to be due to unexpected oxidation of estradiol. Improved cream composition comprises 1% or less 17β-estradiol in the presence of stabilizing members selected from phenolic-type antioxidants, metal chelating agents, and suspending agents.

4 Claims, No Drawings

STABILIZED ESTRADIOL CREAM COMPOSITION

BACKGROUND OF THE INVENTION

It was established decades ago that the principle estrogen of ovulating women is 17β-estradiol. The desirability of achieving a physiologic level of 17β-estradiol in estrogen replacement therapy is obvious. A substantial body of prior art has evolved over this period of time concerning the systemic administration of various estrogenic materials to treat estrogen deficiencies. The oral administration of 17β-estradiol did not come into wide practice until it was made available in a micronized form which improved the solubility of estradiol threby overcoming its poor gastrointestinal absorption. Micronized 17β-estradiol has been given for estrogen replacement therapy by the oral route, cf: Martin, et al, *Obstet. Gynecol.*, Vol. 39, page 771 (1972); and by the intravaginal route, either in the form of an aqueous suspension or solution, cf: Schiff, et al, *Fert. Steril.*, 28/10, 1063–1066 (1977); and Rigg, et al, *J. Clin. Endocr. Metab.*, 45/6, 1261–1264 (1977); or in a cream formulation, cf: Rigg, et al, *New England J. Medicine*, 298/4, 195–197 (1978); Dickerson, et al, *Clin. Pharmacol. Ther.*, 26/4, 502–507 (1979); and Martin, et al, *J. Amer. Med. Assoc.*, 242/24, 2699–2700 (1979). A vaginal cream formulation has some advantage over oral dosage forms for the replacement of 17β-estradiol. Vaginal administration bypasses the ready gastrointestinal conversion of estradiol to estrone. Further, a vaginal cream preparation may be preferred due to other factors including: a different pharmacokinetic profile, patient convenience and comfort, and an added emollient effect of a cream formulation in the treatment of vaginitis, which is a common symptom of estrogen deficiency.

Stability testing of 17β-estradiol vaginal cream formulations identical to those studied by Rigg, et al; Dickerson, et al; Martin, et al; supra. revealed a loss of estrogenic potency with time. This was an unexpected finding inasmuch as there is no teaching in the chemical art that 17β-estradiol lacks stability. Indeed, shelf life studies with solid dosage formulations of estradiol have not revealed stability problems. In addition to loss of estrogenic potency with aging under storage conditions, there was also a deterioration of the physical properties of the cream formulation evidenced by graininess of texture. Therefore, the objectives of this invention were two-fold: to retard loss of estrogenic potency and to maintain physical stability of the cream formulation by devising an improved estradiol cream composition.

SUMMARY OF THE INVENTION

This invention is based in part upon the discovery that 17β-estradiol is chemically stabilized in a cream formulation by the presence of effective amounts of phenolic-type antioxidants and metal chelating agents against unexpected oxidation which is catalyzed by certain metal ions, for example, iron and aluminum cations. Additionally, the physical properties of the cream formulation such as consistency and texture are also stabilized by the use of one or more suspending agents such as the methyl celluloses.

DETAILED DESCRIPTION OF THE INVENTION

The therapeutically-active component of this invention, 17β-estradiol, is a well known and widely used estrogen. An effective concentration range for 17β-estradiol in the compositions of this invention is generally on the order of 1% or less by weight relative to the whole composition. The remainder of the composition is comprised of a pharmaceutically acceptable carrier containing effective concentrations of one or more phenolic-type antioxidants, one or more metal chelating agents, and one or more suspending agents.

Antioxidants used in the instant composition are selected from the group consisting of t-butylhydroquinone, di-t-amylhydroquinone, di-t-butylhydroquinone, butylhydroxytoluene, butylhydroxyanisole, pyrocatechol, pyrogallol, propyl/gallate, and nordihydroguaiaretic acid. The concentration of antioxidant is usually less than 0.1% by weight and preferably about 0.02%. It will also be understood that other antioxidants, not of this preferred group, could also be used in the subject composition.

The metal chelating agents used in the composition consist of ethylenediaminetetraacetic acid (EDTA, edatic acid) or one of its sodium salts, monosodium through tetrasodium EDTA. Calcium disodium EDTA, while not preferred, may also be used. It will also be understood that other chelating agents not of the EDTA group such as dihydroxyethylglycine, citric acid, or tartaric acid could also be used in the subject composition. The preferred metal chelating agent is disodium edetate which is present in a concentration of 0.1% or less, preferably 0.05%, by weight.

For physical stability, 1% or less by weight of the composition is made up of one or more suspending agents selected from the group comprising carbomer, carboxymethylcellulose, hydroxypropyl methylcellulose, and methylcellulose. Preferably, 0.3% by weight of the composition is comprised of hydroxypropyl methylcellulose.

The pharmaceutically acceptable carrier can itself be a composition consisting of oils and/or waxes commonly used in such preparations and emulsified with water utilizing a surfactant as taught by the pharmaceutical arts. These substances are generally in the form of fatty acid esters or fatty alcohols. A preferred carrier composition for the instant invention would be comprised, by weight, of stearyl alcohol ranging from 5–10% of the final cream, glyceryl monostearate ranging from 3–5%, white ceresin wax ranging from 5–10%, propylene glycol ranging from 5–15%, sodium lauryl sulfate ranging from 0.1–0.5% and purified water making up approximately 70% of the total cream.

Stability testing of the compositions of the instant invention confirm retention of estrogenic potency and maintenance of the desired physical properties during six months of storage at temperatures ranging from room temperature to 35° C. Estradiol cream formulations such as those used by Rigg, et al, Dickerson, et al, Martin, et al, supra. prior to the improvement of the instant invention demonstrated texture graininess and potency losses of approximately 25% during storage under similar conditions.

The following example describes in detail a composition of the present invention. It will be apparent to those skilled in the art that many modifications, both of materials and methods, may be practiced without departing from the purpose and intent of this disclosure. From the foregoing description and the following example it is believed that one skilled in the art is able to use the invention to the fullest extent.

EXAMPLE 1

A non-aqueous phase premix is prepared by thoroughly mixing stearyl alcohol (700 g), glyceryl monostearate, non-self-emulsifying (400 g), white ceresin wax 160 (160 signifies the approximate melting point in degrees Fahrenheit; 700 g), and mono-tertiary-butylhydroquinone (2.0 g) while heating to 75° C. Mixing with heating is continued until all solids are dissolved and then 17β-estradiol (1.0 g dry weight) is added. The mixing is then continued until this phase is in the form of a clear solution at which point it is held at 75° for later use.

Propylene glycol (1,000 g) and methylparaben (15 g) are mixed together until all solids are dissolved. Hydroxypropyl methylcellulose 4,000 CPS (CPS refers to centipoise, a designation of viscosity; 30 g) is added to and dispersed in the propylene glycol solution and this resulting mixture is then added to an aqueous solution of disodium edetate (5.0 g) and sodium lauryl sulfate (30 g) in 7,117 g purified water. This mixture is heated and held at 75° while being stirred in order to facilitate the formation of an oil in water emulsion.

The hot non-aqueous phase premix, prepared earlier, is then added to this hot aqueous phase slowly while mixing with an appropriate mixer. If the equipment used permits moisture loss, water may be added during this step to compensate for the loss. The resultant hot emulsion is allowed to cool to 60° C. at which point it is thoroughly homogenized using a recirculating homogenizer, homomixer, or other suitable equipment to provide a particle size reduction to a range of 5–20 microns for most particles. The fluid emulsion, still at 60° C., is passed through a No. 100 to No. 200 stainless steel or nylon screen into a vessel equipped for slow stirring. The emulsion is then cooled while using slow sweep stirring until the temperature reaches 25° C. The equipment employed must be able to thoroughly mix a semi-solid without the incorporation of air. At this point the composition is ready for filling into specified containers.

What is claimed is:

1. A cream composition for topical estrogen therapy which comprises 17β-estradiol of a concentration of about 1% or less on a weight basis relative to the whole composition and the remainder being a pharmaceutically acceptable carrier wherein said carrier contains as stabilizers from about 0.01 to about 10% by weight of at least one member selected from
   (a) one or more phenolic-type antioxidants selected from the group consisting of t-butylhydroquinone, di-t-amylhydroquinone, di-t-butylhydroquinone, butylhydroxytoluene, butylhydroxyanisole, pyrocatechol, pyrogallol, propyl gallate, and nordihydroguaiaretic acid;
   (b) one or more metal chelating agents selected from the group consisting of the sodium edetates (EDTA), and edatic acid; and
   (c) one or more suspending agents selected from the group consisting of carbomer, carboxymethylcellulose, hydroxypropyl methylcellulose and methylcellulose.

2. The composition of claim 1 wherein the concentration of antioxidant is less than 0.1% by weight; the metal chelating agent is a sodium edetate which is present in a concentration of less than 0.1% by weight; at least one of the suspending agents is present in a concentration of 1% or less; and 17β-estradiol is present at a 0.1% or less concentration on a weight basis relative to the whole composition.

3. The composition of claim 1 wherein the antioxidant is tertiary butylhydroquinone at a concentration of 0.2 parts per 1,000 parts cream; the metal chelating agent is disodium edetate at a concentration of 0.5 part per 1,000 parts cream; the suspending agent is hydroxypropyl methylcellulose at a concentration of 3 parts per 1,000 parts cream and 17β-estradiol is at the concentration of 0.1 part per 1,000 parts cream.

4. The composition as recited in claim 3 which further comprises per 1,000 parts cream: stearyl alcohol, 70 parts; glyceryl monostearate, 40 parts; white ceresin wax, 70 parts; sodium lauryl sulfate, 3 parts; methylparaben, 1.5 parts; propylene glycol, 100 parts; and purified water, 712 parts.

* * * * *